United States Patent [19]

Dahan

[11] 4,424,031

[45] Jan. 3, 1984

[54] DENTO-FACIAL ORTHOPAEDY APPARATUS

[76] Inventor: José Dahan, 1, Clos des Dahlias, Kraainem, Belgium

[21] Appl. No.: 360,770

[22] Filed: Mar. 22, 1982

[30] Foreign Application Priority Data

Mar. 24, 1981 [BE] Belgium .............................. 204246

[51] Int. Cl.$^3$ ............................................... A61C 7/00
[52] U.S. Cl. ........................................ 433/18; 433/17
[58] Field of Search ............................ 433/21, 19, 18

[56] References Cited

U.S. PATENT DOCUMENTS 3,936,938 2/1976 Northcutt ............................ 433/21
4,255,139 3/1981 Ladanyl .............................. 433/21

*Primary Examiner*—Robert Peshock
*Attorney, Agent, or Firm*—Cushman, Darby & Cushman

[57] ABSTRACT

There is described a dento-facial orthopaedy apparatus, comprising a force-conveying means at the level of two right-side and left-side molars from a patient, and anchoring means for said conveying means on both said molars in which each anchoring means comprises a fluted tube-like element which is fixedly connected to the one molar, said tube-like element having an axial recess opening outwards through a lengthwise groove, said force-conveying means comprising fastening means which can cooperate with said anchoring means and enter the axial recess from the tube-like elements through the lengthwise groove thereof with a movement along a substantially radial direction relative to the corresponding tube-like element, the apparatus further comprising locking means to prevent any radial movement of the fastening means of the conveying means after entering the tube-like element thereof.

15 Claims, 9 Drawing Figures

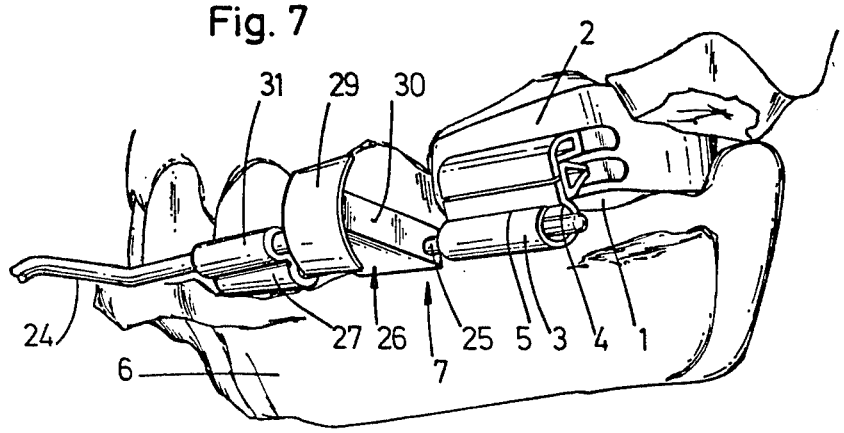
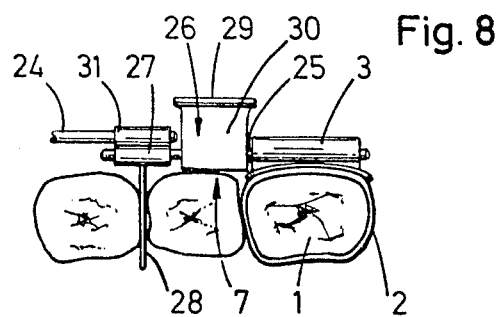
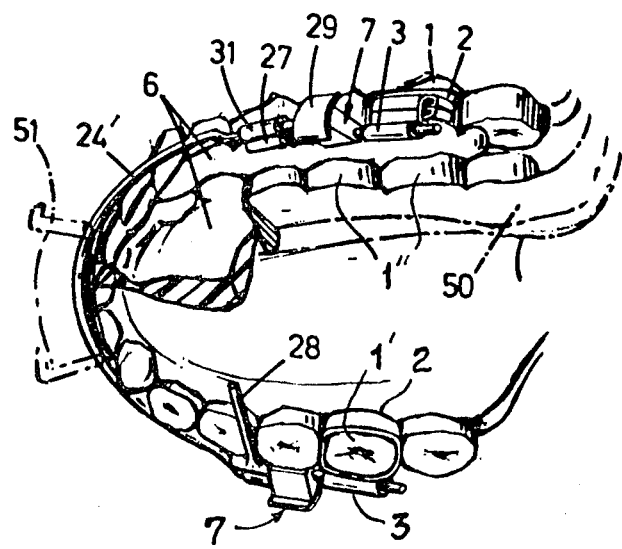

DENTO-FACIAL ORTHOPAEDY APPARATUS

This invention relates to a dento-facial orthopaedy apparatus, comprising a force-conveying means at a level of two right-side and left-side molars of a patient, and anchoring means for said conveying means on both said molars.

Apparatus of this kind has been known for a long time (see notably Belgian Patent No. 873,533), which is designed to convey an orthopaedic or orthodontic force to the upper or lower molars. Said force is generated either through springs or elastic members bearing on the pericranium, that is a so-called artificial or technical force, or by a mandibular movement, that is a so-called muscular or functional force. The technical force has already been studied in all of the biomechanics implications thereof. It is defined in the space direction and magnitude thereof. The results thereof on the tooth are known. Said technical force is generally applied at the level of a dental anchoring device which is welded to a metal ring which surrounds the molar crown. The muscular force which has been less studied than the technical force, is generated by the mandibular movement which causes contracting of the depressor and propulsive muscles, or depressor and retropulsive muscles; such a force is mostly used during the active reaction of the muscles opposing said movements, that is the retropulsive elevator muscles or the propulsive elevator muscles. Said muscles contract isometrically without mandibular movement due to a bimaxillary orthopaedy apparatus which locks the mandibular condition.

All of said apparatus have however the drawback that the securing of an endobuccal or exobuccal orthopaedy apparatus on the molars is generally very intricate. For the patient himself and even more for someone else, it is very difficult to enter, by lengthwise sliding, the ends of the fastening members of such apparatus into the front opening of the hollowed casings which are made fast on the vestibule side on the molar crowns by a ring.

This invention has an object to design a dento-facial orthopaedy apparatus to the above-defined type, which allows securing easily an endobuccal and/or exobuccal orthopaedy apparatus on the right-side and left-side molars of the upper and lower jaws, and this by the patient himself or someone else.

There is provided according to the invention, a dento-facial orthopaedy apparatus as defined hereinabove, in which each anchoring means comprises a fluted tube-like element which is fixedly connected to one molar, said tube-like element having an axial recess opening outwards through a lengthwise slot or groove. Said force-conveying means comprises fastening means which can cooperate with said anchoring means and enter the axial recess of the tube-like elements through the lengthwise groove thereof with a movement along a substantially radial direction relative to the corresponding tube-like element. The apparatus further comprises locking means to prevent any radial movement of the fastening means of the conveying means after entering the tube-like element.

According to a particular embodiment of the invention, said axial recess in the tube-like element also opens outwards through a front end opening and possibly also through a back end opening, which enables lengthwise sliding of the corresponding fastening member of the force-conveying means into the or out of the axial recess of the tube-like element.

According to a particular embodiment of the invention, the force-conveying means comprises a facial arc the ends of which may, as fastening members, be inserted into said fluted tube-like elements by moving said ends along said radial direction through the lengthwise groove of said tube-like elements.

In another embodiment of the invention, said force-conveying means comprises a bimaxillary orthodontic apparatus and two intermediate left and right members, which are each connected at one end thereof to said bimaxillary apparatus, the other end of each intermediate member being insertable, as a fastening member, into one of said fluted tube-like elements by moving same along said radial direction through the lengthwise groove of the element.

According to another advantageous embodiment of the invention, each intermediate member is provided with an operating element on the vestibule side, to let the patient control the movement along said radial direction of said intermediate members.

Other details and features of the invention will stand out from the following description, given by way of non limitative example and with reference to the accompanying drawings, in which:

FIG. 7 is a perspective view similar to FIG. 1, of a variation of the apparatus.

FIG. 8 is a bottom view of the apparatus as shown in FIG. 7, the bimaxillary apparatus not being shown for clearness sake.

FIG. 9 is a perspective view toward the undersigned of the upper teeth illustrating the apparatus shown in FIG. 7 attached to both left side and right side upper molars and to the bimaxillary apparatus. Only a left portion of the bimaxillary apparatus is shown along with a portion of the left inferior jaw (in dot-dash lines) carrying several teeth.

In the various figures, the same reference numerals pertain to similar components.

Figure 1:
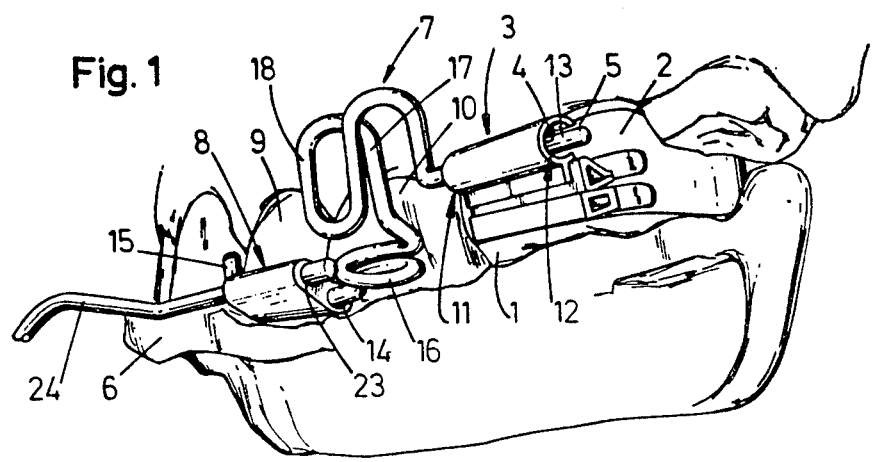
FIG. 1 is a perspective view of an embodiment of an apparatus according to the invention.

The dento-facial orthopaedy apparatus shown in FIG. 1 comprises a force-conveying means at the level of anchoring means provided on two upper molars, one left-side 1 and one right-side 1'. Only the left side molar 1 is shown in FIG. 1, but both molars 1 and 1' are shown in FIG. 9, along with several lower left-side molars 1" in jaw 50.

The anchoring means as shown comprises a metal ring 2 surrounding the crown of said molar 1 and provided on the vestibule side with a fluted tube-like element 3 fixedly secured to said ring. Said tube-like element 3 has an axial recess 4 opening outwards through a lengthwise slot or groove 5. In the case shown, said recess also opens outwards through front and back end openings 11 and 12.

The force-conveying means comprises in the case as shown, a bimaxillary orthodontic apparatus 6 of occluding resin 7, and two intermediate left and right members, but one of which is shown in FIG. 1 but both in FIG. 9. Each member 7 comprises an operating member which will be further described hereinbelow, which is hingedly connected at one end thereof to a hinging element 8 anchored in the occluding resin of the orthodontic apparatus 6 between both pre-molars 9 and 10.

The lengthwise groove 5 is so arranged as to allow fitting the free end 13 of the intermediate member 7 inside the axial recess 4 of the tube-like element 3 by moving said end 13 along a radial direction relative to the tube-like element 3 through said groove 5. On the other hand, once said end 13, used as a fastening member cooperating with the anchoring means, is fitted inside the tube-like element, it should be retained against any motion along a vertical direction. Consequently said groove 5 opens sidewise from recess 4, that is the edges are preferably provided on either side of a horizontal plane, and the tube-like element walls prevent a movement of said end 13 in the occlusion or cervical direction. On the other hand, said end 13 can still slide frontwards and/or backwards, and may thus be removed from the tube-like element by a simple pulling frontwards.

The displacement along a radial direction of intermediate member 7 is obtained by means of the hinging element 8 which is connected to the operating member for said intermediate member 7 by means of a socket 14 to let the end 15 of said operating member rotate about the axis thereof by having the free end 13 thereof follow an arc of a circle which passes through said lengthwise groove 5.

Figure 2:
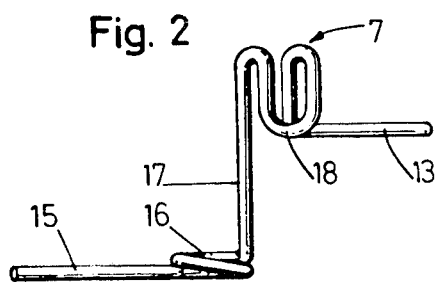
FIG. 2 is a perspective view of the intermediate member of the apparatus as shown in FIG. 1.
Figure 3:
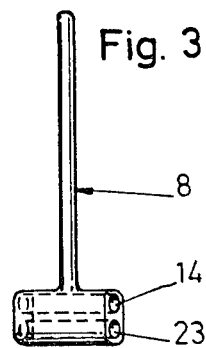
FIG. 3 is a perspective view of the hinging element of the intermediate member as shown in FIG. 2.

The intermediate member 7 is comprised in the case as shown in FIGS. 1 and 2, of the hinging element 8 and a resilient wire, used as an operating member. With said intermediate member 7 in fastening condition inside tube-like member 3, said wire comprises a horizontal portion 15 which is rotatable inside socket 14 and which is possibly curved back at the end thereof to prevent any sliding backwards, a winding 16 giving resiliency in a vertical direction, an upright leg 17 used to compensate the level differential between socket 14 and tube-like element 3, and the end 13 driven radially down in groove 5. Between leg 17 and end 13, there may be provided a U-shaped loop 18 which is possibly bent hook-like in the vestibule direction, such loop making easier that operation allowing the patient to control by hand the positioning of the intermediate member 7. It is to be noted that said intermediate member 7 insures some resiliency, to the exception of a resiliency in sagittal direction, to minimize the force being conveyed to the molars.

Once end 13 has been fitted into axial recess 4 of tube-like element 3, said end should be locked therein to prevent performing a radially-directed motion as the apparatus is being used. In the embodiment as shown in FIG. 1, the lengthwise edges of groove 5 have resilient memory properties and are mutually spaced by a distance which is shorter than the thickness of said end 13. By pressing radially the intermediate member, said lengthwise edges spread to let said member end 13 pass into axial recess 4 and they come nearer automatically thereafter due to said resilient properties to lock in the radial direction said intermediate member inside the recess.

Figure 4:
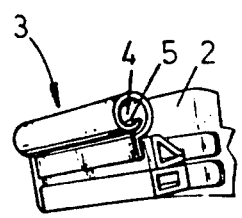
FIGS. 4 to 6 show various embodiments of a fluted tube-like element anchored on the molar.

In the embodiment as shown in FIG. 4, the edges of groove 5 may overlie one another to lock in the radial direction said intermediate member end 13 inside recess.

Figure 5:
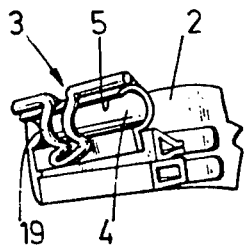

In the embodiment as shown in FIG. 5, the locking means of the groove comprises a spring element 19 which partly closes said groove 5 and may be moved away for a time from tube-like element 3 against the return force of spring element 19 which lets end 13 enter said axial recess 4.

Figure 6:
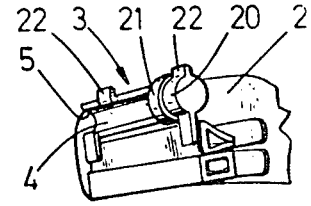

In the embodiment as shown in FIG. 6, the tube-like element 3 is not fluted or slotted over the whole length thereof, which allows reinforcing said part, the back end 20 thereof being made solid and the back opening closed. Over the tube-like element is slidable a ring-like element 21, between a back position which uncovers groove 5 and a center position which enables locking along the radial direction, said end 13 inside axial recess 4. Stops 22 are provided to limit the stroke of ring-like element 21.

As it appears from FIGS. 1 and 2, said hinging element 8 may comprise besides the socket 14, at least one additional socket 23 for fastening the end of a leg 24 of a facial arc 24', as shown in FIG. 9. The arc may have connections 51 with optional known exobuccal orthopaedy apparatus (not shown).

In the embodiment as shown in FIGS. 7 and 8, each intermediate member 7 comprises a wire 25, which is now straight, and an operating member 26 secured to said wire on the vestibule side. The wire 25 is so shaped as to be slightly resilient in the radial direction and it is fixedly secured inside a socket 27 which is arranged on a support 28 anchored in the bimaxillary orthodontic apparatus 6. The fluted tube-like element 3, made fast to ring 2, and the socket 27 lie in this embodiment substantially at the same level, in such a way that the wire 25 after a slight radial bending with the operator's finger on the operating member 26 will be able to enter the axial recess 4 in fluted element 3 by moving along the radial direction through the lengthwise groove 5 thereof. The operating member comprises in this embodiment as shown, a small plate 30 projecting sidewise relative to wire 25, the free end thereof being covered by a protecting strip 29, which is advantageously curved inwards to protect the user's cheek. A socket 31 may be additionally provided on support 28 for receiving a leg 24 of a facial arc.

It must be understood that the invention is in no way limited to the above embodiments and that many changes may be brought therein without departing from the scope of the invention as defined by the appended claims.

It is clear that the fluted tube-like element may be provided with any known locking means which opposes a radial movement of the end from the force-conveying means.

The force-conveying means may in some cases be comprised but of a leg of a facial arc the ends of which are fitted directly inside the fluted tube-like elements, or else of any other means enabling to convey a functional and/or technical force.

The intermediate member may of course be provided with a different shape and/or hinge and/or fastening.

It is clear that the axial recess of the tube-like element may have any cross-section shape, for example a circle-like, square or other shape, depending on the cross-section shape of the fastening means for the force-conveying means.

It is moreover possible to consider connecting the radial locking means not directly to the tube-like element, but rather for example to the fastening means proper from the force-conveying means.

I claim:

1. A dento-facial orthopaedy apparatus comprising:

force-conveying means at the level of two right-side and left-side molars;

anchoring means for said force-conveying means on both said molars;

each of said anchoring means comprising a tube-like element fixedly connected to one of said molars, said tube-like element being provided with an axial recess outwards opened through a lengthwise groove;

said force-conveying means comprising fastening means cooperating with each of said anchoring means, each fastening means being movable in a substantially radial direction relative to the corresponding tube-like element independently of the remaining portion of said force-conveying means, and being so entered in said axial recess of said tube-like element through the lengthwise groove thereof; and locking means to prevent any radial movement of the fastening means of the force-conveying means after entering their tube-like element.

2. Apparatus as defined in claim 1, in which said axial recess in the tube-like element also opens outwards through a front end opening and possibly also through a back end opening, which enable lengthwise sliding of the corresponding fastening member from the force-conveying means into the or out of the axial recess of the tube-like element.

3. Apparatus as defined in claim 1 in which in the locking position of the force-conveying means, the tube-like element walls prevent a vertical motion of the corresponding fastening means of the force-conveying means.

4. Apparatus as defined in claim 1 in which the lengthwise groove edges are provided on either side of a horizontal plane.

5. Apparatus as defined in claim 1 in which said locking means are comprised of the lengthwise edges from said lengthwise groove which have resilient-memory properties and which under the radial pressure of the corresponding fastening member from the force-conveying means, spread from one another to let said means enter the axial recess of the tube-like element and then come nearer one another under the action of said resilient-memory properties to thus lock radially said fastening member inside said recess.

6. Apparatus as defined in claim 1 in which said locking means are comprised of a spring element which closes partly at least said groove and which may be moved temporarily away from the tube-like element against the return force thereof, to thus open said groove.

7. Apparatus as defined in claim 1 in which said locking means are comprised of an element which is slidable over the tube-like element between a position where it overlays but the endmost portion from said tube-like element, and a center position for locking radially the fastening member of the force-conveying means.

8. Apparatus as defined in claim 1, in which the force-conveying means comprises a facial arc the ends of which may as fastening members, be inserted into said fluted tube-like elements by moving said ends along said radial direction through the lengthwise groove of said tube-like elements.

9. Apparatus as defined in claim 1, in which said force-conveying means comprises a bimaxillary orthodontic apparatus and two intermediate left and right members, which are each connected with the one end thereof to said bimaxillary apparatus, the other end from each intermediate member being insertable as fastening member, into the one said fluted tube-like elements by moving same along said radial direction through the lengthwise groove thereof.

10. Apparatus as defined in claim 9, in which each intermediate member is provided with an operating element on the vestibule side, to let the patient control the movement along said radial direction of said intermediate members.

11. Apparatus as defined in claim 10, in which the operating member for each intermediate member is hingedly connected to the bimaxillary apparatus, to be swingable along said radial direction when the bimaxillary apparatus lies in position inside the mouth.

12. Apparatus as defined in claim 11, in which each operating member comprises a wire connected to the bimaxillary apparatus, in such a way as to be able to perform said swinging motion, through a hinging element which is anchored in said bimaxillary apparatus, said wire being so arranged as to have some resiliency to the exception of a resiliency in the sagittal direction.

13. Apparatus as defined in claim 12, in which in the position where the intermediate member is fitted into the tube-like element, said wire comprises back of the end thereof connected to a swinging socket from said hinging element, a horizontal winding which is extended with a vertical leg of the length of which is at least equal to the level differential between said hinging element and said fluted tube-like element, said vertical leg being extended with a U-shaped loop, which is possibly bent hook-like, the free leg thereof being bent back along the axis of the tube-like element.

14. Apparatus as defined in claim 13, in which each hinging element comprises besides said swinging socket, at least one additional socket for receiving therein the one end from a facial arc which is provided as additional force-conveying means.

15. Apparatus as defined in claim 10, in which said intermediate member comprises a straight wire, resilient in the radial direction, which is fixedly secured with the one end thereof, into a socket anchored in the bimaxillary orthodontic apparatus, and said operating member fastened to said wire on the vestibule side, and said socket and fluted tube-like element are arranged at the same level on the jaw, in such a way that said radial motion of the wire inside the grooved element be obtained with a slight resilient distortion of said wire.

* * * * *